United States Patent [19]

Kubiatowicz

[11] 4,323,055
[45] Apr. 6, 1982

[54] RADIOACTIVE IODINE SEED

[75] Inventor: David O. Kubiatowicz, White Bear Lake, Minn.

[73] Assignee: Minnesota Mining and Manufacturing Company, St. Paul, Minn.

[21] Appl. No.: 138,293

[22] Filed: Apr. 8, 1980

[51] Int. Cl.³ ............................................. A61K 27/04
[52] U.S. Cl. ...................................... 128/1.2; 424/1; 424/1.5
[58] Field of Search .................. 128/1.2; 424/4, 1, 1.5

[56] References Cited

U.S. PATENT DOCUMENTS

| | | | |
|---|---|---|---|
| 1,718,899 | 6/1929 | Fischer | 128/1.2 |
| 3,351,049 | 11/1967 | Lawrence | 128/1.2 |
| 3,663,685 | 5/1972 | Evans | 424/1 |
| 4,101,646 | 7/1978 | Sugimoto | 424/4 |

OTHER PUBLICATIONS

Merck Index, 9th edition, 1976, pp. Misc-16 & 17.
Kirk-Othmer, Encyclopedia of Chemical Technology, vol. 18, p. 296.

*Primary Examiner*—Robert W. Michell
*Assistant Examiner*—Nancy A. B. Swisher
*Attorney, Agent, or Firm*—Cruzan Alexander; Donald M. Sell; Carolyn A. Bates

[57] ABSTRACT

Improved radioactive iodine seeds are disclosed wherein the carrier for the radioisotope is a rod-like member which is detectable by X-rays and occupies a substantial portion of the space within the seed.

6 Claims, 1 Drawing Figure

U.S. Patent  Apr. 6, 1982  4,323,055
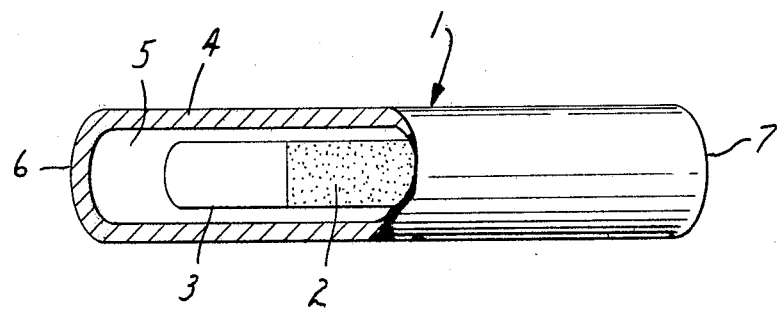

RADIOACTIVE IODINE SEED

This invention relates to improved radioactive iodine "seeds" for use in radiation therapy of diseased tissue.

Radioactive iodine seeds are known and described by Lawrence in U.S. Pat. No. 3,351,049. The seeds described therein comprise a tiny sealed capsule having an elongate cavity containing the radioisotope adsorbed onto a carrier body. The seeds are inserted directly into the tissue to be irradiated. Because of the low energy X-rays emitted by iodine-125 and its short half-life, the seeds can be left in the tissue indefinitely without excessive damage to surrounding healthy tissue or excessive exposure to others in the patient's environment.

In addition to the radioisotope and carrier body, the container also preferably contains an X-ray marker which permits the position and number of seeds in the tissue to be determined by standard X-ray photographic techniques. This information is necessary in order to compute the radiation dose distribution in the tissue being treated. The Lawrence patent illustrates two methods of providing the X-ray marker. In one embodiment, there is provided a small ball of a dense, high-atomic number material such as gold, which is positioned midway in the seed. The radioisotope is impregnated into two carrier bodies located on either side of the ball. In the other embodiment, the X-ray marker is a wire of a high-atomic number dense material such as gold located centrally at the axis of symmetry of a cylindrical carrier body. The carrier body is impregnated with the radioisotope and is preferably a material which minimally absorbs the radiation emitted by the radioisotope.

In recent years iodine-125 seeds embodying the disclosure of the Lawrence patent have been marketed under the tradename "3M Brand I-125 Seeds" by Minnesota Mining and Manufacturing Company, the assignee of the present application. These seeds comprise a cylindrical titanium capsule containing two Dowex ® resin balls impregnated with the radioisotope. Positioned between the two resin balls is a gold ball serving as the X-ray marker. These seeds suffer from several disadvantages. Firstly, the gold ball shows up as a circular dot on an X-ray film, and does not provide any information as to the orientation of the cylindrical capsule. This reduces the accuracy with which one can compute the radiation pattern around the capsule. Another disadvantage of using three balls inside the capsule is that they tend to shift, thereby affecting the consistency of the radiation pattern. A further disadvantage of the prior art seeds lies in their manufacture. Since the resin balls and the gold X-ray marker are inserted into the capsule manually, careful attention must be paid in order to insure that each capsule contains two balls and that the gold marker is in the center. Because the possibility of human error is quite high in this type of assembly, a significant number of seeds are improperly assembled and must be rejected during quality control inspection.

The radioactive iodine seeds of the present invention uniquely overcome the aforementioned problems associated with presently available radioactive seeds. According to the present invention, there is provided an improved radioactive iodine seed comprising a sealed container having an elongate cavity, a therapeutic amount of radioactive iodine within the cavity, and a carrier body disposed within the cavity for maintaining the iodine in a substantially uniform distribution along the length of the cavity, characterized by the improvement wherein the carrier body is an elongate rod-like member which is detectable by X-rays and occupies a substantial portion of the space within the cavity.

Since the carrier body functions both as the carrier for the isotope and the X-ray marker, the capsule filling step of the manufacturing process is greatly simplified, involving the insertion of a single component. Furthermore, since the carrier body conforms to the shape of the capsule, the exact location and orientation of the seed in the tissue can be determined from X-ray photographs.

Other advantages and features of the invention will be apparent from the following description and from the accompanying drawing which illustrates a greatly enlarged view of the iodine seed with portions thereof partially broken away.

The seed 1 comprises a therapeutic amount of radioactive iodine 2 appropriately distributed on a carrier body 3 disposed in cavity 5 of a tubular container 4. The container 4 is sealed at ends 6 and 7 and serves to isolate the radioisotope from physical or chemical interchange between body fluids and the interior of the container, while at the same time permitting the radiation to pass through the walls of the container with minimum attenuation.

As is taught by the prior art, when selecting a suitable material for the container, one should strive for the optimum balance between maximum mechanical strength of the container and minimum absorption characteristics of the wall. The prior art applied this principle and concluded that low atomic numbered metals such as stainless steel alloy or titanium work well for this purpose. Higher atomic number metals such as gold or platinum result in too much radiation attenuation to be useful per se. However, they may be useful as a plating over certain low atomic number materials such as beryllium which would otherwise be too toxic if used without an outer coating.

Titanium, having a low atomic number and high strength-to-weight ratio, is the presently preferred material for the container. It is exceptionally corrosion-resistant and very satisfactory from the standpoint of tissue compatibility and nontoxicity. Titanium should be selected as a rather pure alloy to assure good working characteristics. The wall thickness of the titanium may vary from 0.001 to 0.005 inch (0.025 to 0.127 mm), the attenuation being about 7% per thousandths of an inch. An optimum value of wall thickness is approximately 0.002 inch (0.051 mm).

The ends of the titanium container can be sealed by various techniques, such as laser, electron beam or TIG (tungsten inert gas) welding.

Container 4 is preferably designed for implantation by perforate penetration or injection, e.g., by hypodermic needle or similar device especially designed therefor. As such, the container 4 is preferably constructed in an elongated shape, having a relatively narrow outer diameter of from about 0.5 to 1 millimeter, and about 4–5 millimeters in length. The interior of the container 4 includes a cavity 5 for receiving the carrier body 3, as hereinafter described. For permanent implantation, as by hypodermic injection, the outside diameter of the seed is preferably about 0.80 millimeter and is thus small enough to pass through a 17 gauge hypodermic needle. The seed is constructed approximately 4 to 5 mm long.

It exhibits minimal movement in the tissue and does not migrate from the area to be treated.

The essence of the present invention resides in improved carrier body 3 which is itself detectable by X-rays as well as serving as the solid support for the radioactive iodine. Carrier body 3 insures that the radioisotope is substantially evenly distributed throughout the length of the container and that it does not shift or migrate during use.

Carrier body 3 may be constructed of any material which is detectable by X-rays and to which the requisite therapeutic amount of iodine-125 can be attached. The present material of choice is a silver rod of suitable length and diameter to permit it to be easily inserted into container 4 and occupy a substantial portion of cavity 5. The silver rod is preferably about 3 mm long and 0.5 mm in diameter when used in a standard titanium container having a length of 4.5 mm and an exterior diameter of 0.8 mm. A 3 mm long rod results in minimum shifting within the container while allowing adequate room to weld the ends of the container without involving the silver rod. The diameter of the rod can range from 0.10 mm to about 0.70 mm (the maximum inside diameter of the conventional titanium container). The preferred diameter is about 0.5 mm since this size provides good X-ray visibility, is relatively easy to handle during the filling operation and slides easily into the container without abrading against the interior walls of the container.

Silver is the material of choice for carrier body 3 because it provides good X-ray visualization and because radioactive iodine can be easily attached to the surface thereof by chemical or electroplating processes. It is obvious that other X-ray opaque metals such as gold, copper, iron, etc., can be plated with silver to form a carrier body equivalent to a solid silver rod for purposes of the present invention. Likewise, silver metal can be deposited (chemically or by using "sputtering" and "ion plating" techniques) onto a substrate other than metal, e.g., polypropylene filament, provided that the thickness of the silver coating on the substrate exceeds about 0.050 mm to insure X-ray visualization.

Radioactive iodine can be attached to a silver surface by first chloriding or bromiding the silver to form a layer of insoluble silver chloride or silver bromide, and then replacing the chloride or bromide ions with radioactive iodide ions by simple ion exchange.

Silver halides are some of the most water-insoluble salts known. Solubility decreases as the silver halides progress from the chloride to the iodide salt as shown by the following solubility product ($K_{sp}$) values:

| Salt | Ksp (25° C.) |
|------|---------------|
| AgCl | $1.56 \times 10^{-10}$ |
| AgBr | $7.70 \times 10^{-13}$ |
| AgI  | $1.50 \times 10^{-16}$ | where generally $K_{sp}=[M^+][A^-]$ and where specifically $[M^+]$ is the concentration of silver ions $[Ag^+]$ and $[A^-]$ is the concentration of halide ions $[Cl^-]$, $[Br^-]$ or $[I^-]$ in moles/liter. A more insoluble salt in a series will tend to form if the requisite halide anion is present. For example, yellowish AgBr will form if $Br^-$ anion is added to a solution containing precipitated white AgCl. Similarly, yellow AgI forms upon the addition of $I^-$ anion to solutions containing precipitates of either AgCl or AgBr.

This is the basis upon which radioactive iodide ($^{125}I^-$) is exchanged with either AgBr or AgCl adsorbed on the silver wire. Salt insolubility is important in order to minimize the amount of "free" iodine-125 anion in the reaction supernatant. This insolubility is necessary to get the required deposition on the surface of the rod.

Water-insoluble metal halide salts other than silver halide salts, e.g., copper halides (CuCl, CuBr and CuI), gold halides (AuBr, AuI), some palladium halides ($PdBr_2$) and some platinum halides ($PtBr_2$ and $PtI_2$) are known. This suggests that carrier bodies of copper, gold, palladium, platinum, etc. could be used in the practice of the present invention. However, halide salts of these metals are more soluble than those of silver and precipitate forms are thus more difficult to form. Also, they tend to be more toxic, some are oxidized by air, and others are unstable to heat. Thus, silver or silver-plated rods are preferred.

Many metal halides, especially silver halides, are light-sensitive. The metal ion is reduced to metal (photoreduction) and the halide anion is oxidized to free halogen. Among the silver halides, silver bromide is the most light-sensitive, followed by silver chloride and silver iodide, respectively. For this reason, in an ion-exchange process for coating the silver wire with iodine-125 according to the present invention, silver bromide is less preferred than silver chloride as the precursor. Silver bromide will, however, provide an acceptable precursor provided means are taken to minimize exposure to visible blue and ultraviolet light. Since silver iodide is also somewhat light-sensitive, it is desirable to minimize exposure of the silver rods containing adsorbed iodine-125 to visible blue or UV light prior to encapsulation within the titanium container. This can be done by working under "safe" lights, e.g., red or yellow lights.

The precursor silver chloride or silver bromide layer can be formed on the silver rod using conventional chemical or electroplating processes. The presently preferred method of chloriding or bromiding the silver rod is a chemical plating process wherein the silver rods are placed in an aqueous solution of an oxidizing agent containing chloride or bromide anion.

A number of oxidizing agents will cause silver chloride, for example, to be formed on the surface of the silver rod provided that the reaction conditions allow an oxidation-reduction reaction to occur in which silver metal loses one electron to become $Ag^+$ and a chloride anion ($Cl^-$) is available to form insoluble silver chloride (AgCl).

Whether or not a particular reaction will occur spontaneously in this respect can be predicted by reference to a standard table of half-cell electromotive force (emf) values (i.e., oxidation-reduction potentials as found in: Latimer, W. M., *The Oxidation States of Elements and Their Potentials in Aqueous Solution*, 2nd edition, New York: Prentice-Hall, Inc., 1952). Any reaction will occur spontaneously if the sum of the emf values for the oxidation half-reaction and the reduction half-reaction is positive.

For example, the preferred oxidation agent for use in chloriding the silver rods is sodium chlorite ($NaClO_2$). When sodium chlorite is added to acid solution, it disproportionates into a reduced species, hypochlorous acid (HOCl), and an oxidized species, chlorine dioxide ($ClO_2$). Both of these species are capable of oxidizing silver as shown below.

| Half-Cell Reaction | Acid emf (volts) |
|---|---|
| (1) oxidation Ag → Ag$^+$ + e$^-$ | −0.80 |
| reduction ClO$_2$ + e$^-$ → ClO$_2^-$ | 1.16 |
| (2) net Ag + ClO$_2$ → Ag$^+$ + ClO$_2^-$ | 0.36 |
| oxidation Ag → Ag$^+$ + e$^-$ | −0.80 |
| reduction HOCl + H$^+$ + 2e$^-$ → Cl$^-$ + H$_2$O | 1.49 |
| net Ag + HOCl + H$^+$ → Ag$^+$ + Cl$^-$ + H$_2$O | 0.69 |

In reaction (1), the chlorine dioxide which was generated from sodium chlorite becomes reduced to again form sodium chlorite in the process of oxidizing silver metal to ionic silver. This reaction proceeds spontaneously with a net reaction potential of 0.36 volts.

Similarly, the hypochlorous acid, also generated from the sodium chlorite, oxidizes silver metal to ionic silver and in the process forms chloride anion (Cl$^-$) with a net reaction potential of 0.69 volts as shown in reaction (2). The generation of chloride (Cl$^-$) in reaction (2) is significant because it continues to react with the ionic silver formed on the surface of the silver rod to produce the desired silver chloride coating.

From the emf values of reactions (1) and (2), one can also predict that hypochlorous acid is capable of oxidizing chlorine dioxide, producing respectively more chloride (Cl$^-$) and chlorate (ClO$_3^-$). Thus, the final reaction products of an acid solution of sodium chlorite in the presence of silver metal appear to be Ag/AgCl, Cl$^-$, and ClO$_3^-$.

In general, in order for the chloriding and bromiding of the silver rod to occur rapidly, it is necessary to add an acid to the reaction solution. If the oxidizing agent itself serves as a source of chloride ions, as is the case with sodium chlorite, (NaClO$_2$) sodium hypochlorite (NaOCl), and chlorine gas (Cl$_2$), an acid having no available halogen atoms such as acetic acid, phosphoric acid or sulfuric acid may be used. However, hydrochloric or hydrobromic acid is preferred because the availability of extra halide ion speeds the formation of silver halide ions. When the oxidizing agent does not provide the requisite halide, hydrochloric or hydrobromic acid is conveniently used to provide both the desired pH and the halide.

Examples of oxidizing agents other than sodium chlorite which will oxidize the surface of silver rods and, in the presence of either hydrochloric acid (HCl) or hydrobromic acid (HBr) form the surface coatings of silver/silver chloride (Ag/AgCl) or silver/silver bromide (Ag/AgBr) respectively include, but are not limited to: sodium chlorate (NaClO$_3$), sodium chromate (NaCrO$_4$), potassium dichromate (K$_2$Cr$_2$O$_7$) and potassium permanganate (KMnO$_4$).

A sufficient amount of silver chloride or silver bromide must be coated onto the silver wire to insure that when the chloride or bromide is exchanged for radioactive iodide, the seed will provide the requisite radiation. In general, the iodine seed should provide radiation emission which is equivalent to that of between 0.1 and 100 millicuries of radioactivity. To achieve this level of radioactivity, each seed should contain between about 0.15 and 150 millicuries of iodine-125. The additional amount of iodine-125 is required to compensate for approximately 20 percent attenuation by the silver rod (3.0 mm in length and 0.5 mm in diameter) and 14 percent attenuation by the titanium container having a 0.060 mm thick wall.

In the preferred method of chloriding the silver wire, it has been found that an aqueous solution of 6 molar hydrochloric acid (HCl) containing 0.1 molar sodium chlorite (NaClO$_2$) will sufficiently chloride silver rods in approximately 1 hour. The rods are then added to an aqueous solution containing carrier-free iodine-125 for about 18 hours to coat the iodine-125 onto the rods. The supernatant is then withdrawn, and the seeds are washed with acetone and air dried.

Silver chloride or bromide can also be affixed to silver rods using electroplating techniques as described in Examples 1 and 2 below, or radioactive iodine can be electroplated directly onto the silver rods as illustrated in Example 4. These techniques are, however, more cumbersome and generally more time-consuming than the chemical plating process.

After the rods are coated with iodine-125, they are inserted into the open end of the container (one end having been previously sealed), and the container is closed and hermetically sealed in the conventional manner, e.g., TIG welding. (The hermetic seal is required to prevent migration of iodine-125 into the tissue.) The seeds are implanted in the tissue in the conventional manner. The position and the number of seeds in the tissue can be readily determined by X-ray photography. The rod-shaped carrier bodies show up on the X-ray photograph, indicating the precise orientation of the seeds, from which the distribution of the radiation dosage in the tissue can be computed.

The improved radioactive iodine seeds of the invention are further illustrated by reference to the following non-limiting examples.

EXAMPLE 1

Five lengths of silver wire ($\geq 99.9\%$ purity), each 70 mm long and 0.25 mm in diameter, were suspended in a glass graduate containing 25 ml of 1 M NaCl. The lengths of silver wire were attached to the positive (+) electrode of a 6 volt direct current power supply. The negative (−) electrode of the supply was connected to a thin platinum metal strip running along the inside edge of the graduate and in contact with the NaCl. Current of about 0.5 milliampere was applied between the silver wire and platinum electrodes for a period of about 60 minutes. Chloride anions (Cl$^-$) migrated toward the (+) silver wires and reacted with silver cations (Ag$^+$) concurrently formed producing insoluble AgCl on the surface of the silver wires. The wires were weighed to an accuracy of one microgram before and after the application of current. The observed increase in weight (0.7 mg/wire) due to added Cl$^-$ was found to be in agreement with the theoretical weight gain calculated using Faraday's Laws of Electrolysis.

The lengths of silver wire, coated with silver chloride, were cut into about 115 individual lengths of wire each 3 mm long. These were added to a glass test tube (10 mm diameter by 70 mm long) containing 0.2 ml of sodium iodide solution in 0.01 M NaOH. The sodium iodide solution contained less than one microcurie of radioactive iodine-125 and non-radioactive iodide equivalent to about 1000 millicuries of I$^{125}$. (This equivalence can be calculated on the basis that if each atom of iodine is radioactive, then one gram of iodine would contain $1.74 \times 10^4$ curies of iodine-125. Thus, about 57 micrograms of "cold" iodine is "equivalent" to 1000 millicuries of iodine-125). If the seeds were to be used to treat patients, about 100 additional millicuries of iodine-125 would also have been added to this reaction. The test tube was closed and rotated for 17 hours. During this time, radioactive and non-radioactive sodium iodide exchanged with chloride ions on the surface of the wires to form a coating of insoluble silver iodide. Chloride ions were released into solution. Due to the insolubility of silver iodide, substantially all of the iodide originally present in solution reacted with the surface of the wires producing greater than 97% reaction efficiency. This was assessed by measuring the decrease in supernatant radioactivity following the reaction. About 20 percent of the radioactivity absorbed on the surface of the wires was found to be attenuated or absorbed by the wires themselves.

The wires were washed using three 1 ml quantities of acetone, air dried and hermetically sealed (using tungsten inert gas welding) within individual titanium containers about 4.5 mm long, 0.8 mm in diameter and having a wall thickness of about 0.06 mm.

EXAMPLE 2

In this example, individual silver wire rods were plated with silver chloride, eliminating the need to cut silver wire plated with silver chloride. The advantage of this technique is that the ends of the silver rods are also plated, which is not the case with the rods in Example 1. A special electroplating basket (1 inch in diameter by 1¼ inches high) consisting of a titanium support mesh and porous platinum lining was specially fabricated. One hundred silver rods, each 3 mm in length and 0.5 mm in diameter, were placed within the basket, and the basket was submerged in 1 liter of 1 M NaCl. A single platinum strip submerged within the NaCl was attached to the (−) terminal of a 6 volt direct current power supply and the platinum lined basket was connected to the (+) terminal. The basket containing the silver rods was rotated within the NaCl producing a tumbling effect of rods against the platinum wall of the (+) polarized basket while applying a constant current of about 0.5 milliamperes over 6½ hours to achieve approximately the same degree of plating of silver chloride on the surface of the silver rods as described in Example 1.

The silver rods coated with silver chloride were removed from the basket, washed using a small volume of distilled water, rinsed with acetone and air dried. Iodine-125 and non-radioactive iodide were adsorbed onto the surface of the silver-silver chloride rods by ion exchange with chloride and the rods were sealed within titanium containers as described in Example 1.

EXAMPLE 3

In this preferred embodiment of the invention, two thousand silver rods, each having a length of 3 mm and a diameter of 0.5 mm (>99.9% pure metal), were added to a glass vial. Twenty ml of 6 M HCl and 2 ml of 1 M sodium chlorite ($NaClO_2$) were added sequentially to the vial, which was then rotated for one hour at room temperature. The rods, now coated with adsorbed silver chloride, were removed from the glass vial, rinsed well with water, then rinsed with acetone and air dried.

One hundred of these treated silver rods were added to an amber glass vial containing 150 millicuries of iodine-125 (in 0.3 ml of $10^{-4}$ M NaOH solution, pH 10) and non-radioactive iodide equivalent in weight to about 900 millicuries of iodine-125. The function of the non-radioactive iodide in this example was to mix with the radioactive iodine-125 and thus produce a more uniform distribution of iodine-125 on the surface of the individual silver rods.

The vial containing the silver rods and reaction solution was rotated for 19 hours. During this time, more than 97% of the iodine-125 became affixed to the surface of the treated silver rods. The supernatant was withdrawn from the rods. The rods were subsequently washed with acetone, air dried, and encapsulated within titanium containers as described in Example 1. X-ray visibility of the radioactive rods within titanium containers (implanted within raw meat) was excellent, showing the spatial orientation of the rods. Radiation intensity about the exterior of individual titanium containers, as profiled using a crystal diffractometer (having a sodium iodide detector) showed an expected dose pattern and indicated very uniform coating of iodine-125 over the surface of the silver rod inside.

EXAMPLE 4

Eighteen silver wire rods 3 mm long by 0.25 mm in diameter were added to a special glass reaction vial. The vial was 4.5 cm high by 1.5 cm in diameter. It contained a piece of platinum foil which completely covered the inside bottom of the vial and ran up the inside wall and out the top of the vial. This foil was connected to the (+) electrode of a 6 volt direct current power supply. Iodine-125 (18.8 millicuries) in 1.5 ml of dilute NaOH (pH about 10) was added to the vial. A special coiled platinum wire was then inserted into the vial just beneath the surface of the solution and attached to the (−) terminal of the power supply. The reaction vial was agitated using a "maxi-mix" which produced a gentle but rapid motion, causing the silver rods to spin and rotate on the circular platinum foil bottom of the vial. A constant current of 25 microamperes was applied for two hours causing anionic iodine-125 to affix to the surface of the (+)-charged silver rods in contact with the (+)-charged platinum foil. The supernatant solution was removed and the silver rods were washed with small portions of acetone and air-dried.

Several of the rods were placed on X-ray film to assess the distribution of radioactivity on the surface area. The film disclosed uniform distribution. In addition, X-rays of the rods showed good radiographic visualization. The rods were sealed within titanium containers as described in Example 1.

What is claimed is:

1. In a radioactive iodine seed comprising a sealed container having an elongate cavity, a therapeutic amount of radioactive iodine within said cavity and a carrier body disposed within said cavity for maintaining said radioactive iodine in a substantially uniform distribution along the length of said cavity, the improvement wherein said carrier body is an elongate rod-like member formed of silver or a silver-coated substrate which is X-ray detectable, said carrier body containing a layer of radioactive iodide formed on the surface of said carrie body, said carrier body occupying substantial portion of the space within said cavity.

2. The radioactive iodine seed according to claim 1 wherein said carrier body is a silver rod.

3. The radioactive iodine seed according to claim 2 wherein said silver rod is about 0.10 to 0.70 mm in diameter.

4. The radioactive iodine seed according to claim 3 wherein said silver rod is about 3 mm in length.

5. The radioactive iodine seed according to claim 1 having radiation emission equivalent to that of between about 0.1 to 100 millicuries of radioactivity.

6. The radioactive iodine seed according to claim 1 wherein said container comprises titanium.

* * * * *